United States Patent [19]
Orsak et al.

[11] Patent Number: 5,792,076
[45] Date of Patent: Aug. 11, 1998

[54] FRACTURE CONSOLIDATION MEASURING APPARATUS

[75] Inventors: James E. Orsak, Memphis; Abraham B. Salehi, Bartlett, both of Tenn.

[73] Assignee: Smith & Nephew, Inc., Memphis, Tenn.

[21] Appl. No.: 586,998

[22] Filed: Jan. 16, 1996

Related U.S. Application Data

[63] Continuation-in-part of Ser. No. 373,602, Jan. 17, 1995, Pat. No. 5,695,496.
[51] Int. Cl.$^6$ ............................................. A61B 5/103
[52] U.S. Cl. ............................................. 600/587; 606/59
[58] Field of Search ........................ 606/52, 53, 54, 606/59, 62, 63, 86, 102; 600/587

[56] References Cited

U.S. PATENT DOCUMENTS

| | | | |
|---|---|---|---|
| 4,191,470 | 3/1980 | Butter | 356/35.5 |
| 4,576,158 | 3/1986 | Boland | 128/92 R |
| 4,841,778 | 6/1989 | Butler et al. | 73/800 |
| 4,913,137 | 4/1990 | Azer et al. | 606/64 |
| 5,454,810 | 10/1995 | Pohl et al. | 606/59 |

FOREIGN PATENT DOCUMENTS

1623628 1/1991 U.S.S.R.

*Primary Examiner*—Max Hindenburg
*Assistant Examiner*—Pamela L. Wingood
*Attorney, Agent, or Firm*—Pravel, Hewitt & Kimball

[57] ABSTRACT

Apparatus for measuring bone strain to detect fracture consolidation includes a fixation device which is affixed to a patient's bone that has a fracture site to be healed and wherein the fixation device supports an elongated optical fiber. Light is transmitted through the optical fiber to an exit point. The light intensity within the optical fiber is measured, preferably at the exit point as the light travels through the optical fiber. Light intensity is measured to monitor strain in the fixation device as the fracture site heals. A physician then determines when the site has fully healed by observing changes in light intensity as the patient's bone rather than the fixation device carries more of the patient's normal body loading.

20 Claims, 8 Drawing Sheets

FRACTURE CONSOLIDATION MEASURING APPARATUS

CROSS REFERENCE TO RELATED APPLICATIONS

This is a continuation-in-part of U.S. patent application Ser. No. 08/373,602, filed Jan. 17, 1995, now U.S. Pat. No. 5,695,496 which is incorporated herein by reference.

BACKGROUND OF THE INVENTION

1. Field of the Invention

The present invention relates to surgical orthopedic instrumentation and to the external fixation of bone fractures. More particularly, the present invention relates to an improved method and apparatus for determining the extent of healing of a bone fracture that is supported during the healing process by an external fixation device. Even more particularly, the present invention relates to an improved method and apparatus for measuring bone strain after a bone has been fractured and is supported during the healing process with a surgically attached external fixation and wherein an external fixation device carries one or more light transmitting elements (such as an optical fiber), and light intensity transmitted through the optical fiber is measured to determine whether or not the patient's bone has fully healed to carry normal loading generated by the patient (such as the weight of the patient).

2. General Background

One of the major questions presented to a surgeon after treating a bone deformity or problem fracture is the question of bone healing. Specifically, the surgeon needs to know whether or not the healing is complete. Physicians are frequently presented with the question of when can a cast, plate, screw or external fixation device be removed. If the doctor continues treatment longer than necessary, the patient can be subjected to undue discomfort. If the doctor prematurely removes such a device, there is a risk of refracture.

Currently, physicians use an x-ray of the fracture site to make a decision regarding the extent of healing of a bone fracture. However, x-rays do not always give a clear and accurate assessment. Often physicians are forced to make judgment calls regarding the degree of healing at a fracture site.

External fixation devices for setting bone fractures are known in the art. One example is U.S. Pat. No. 4,576,158 entitled "Method For Determining Stability of an Orthopedic Device Composed of an External Fixation Bar During Setting of Bone Fractures", issued to Michael Boland. In the Boland patent, the stability of an orthopedic assembly characterized by external fixation means in the form of a fixation bar provided with five assemblies of strain gauges having at least one gauge each, involves a measuring of the amount of torsion of the bar by one of the assemblies and measuring of two perpendicular components of the amount of bending of the bar at two points of the bar via the remaining two pairs of assemblies and determining by means of the strain gauges the amount of torsion and the amount of bending at the level of the clamps which connect the fixation bar to the pins and by comparison of the determined levels of the torsion and bending with those capable of causing sliding of the clamps, the extent of stability of the orthopedic assembly.

Patents have been issued which describe the use of fiber optics as part of a strain gauge. These include U.S. Pat. No. 4,191,470 issued to C. D. Butter and U.S. Pat. No. 4,841,778 issued to M. A. Butler. The Butter patent is directed to a laser-fiber optic interferometric strain gauge. This is a strain gauge that can be read out by means of fiber optics, which has no power other than optical at the strain gauge. Laser light is directed into two single mode fibers, which fibers are attached to a supporting member, the strain gauge of which is to be measured. The ends of the fibers are brought into close proximity and the light coming out of the two fibers interferes. When the supporting member is strained, the fringes move giving a measure of the strain.

In the Butler patent, (U.S. Pat. No. 4,841,778), laser light from a common source is split and conveyed through two similar optical fibers and emitted at their respective ends to form an interference pattern, one of the optical fibers having a portion thereof subjected to a strain. Changes in the strain cause changes in the optical path length of the strain fiber, and generate corresponding changes in the interference pattern. The interference pattern is received and transduced into signals representative of fringe shifts corresponding to changes in the strain experienced by the strained one of the optical fibers. These signals are then processed to evaluate strain as a function of time. Typical examples of the application of the apparatus include electrodeposition of a metallic film on a conductive surface provided on the outside of the optical fiber being strained, so that strains generated in the optical fiber during the course of the electrodeposition are measurable as a function of time. In one aspect of the invention, signals relating to the fringe shift are stored for subsequent processing and analysis, whereas in another aspect of the invention the signals are processed for real-time display of the strain changes under study.

SUMMARY OF THE PRESENT INVENTION

The present invention provides a doctor with a diagnostic tool to aid in the assessment of the degree of healing of a fractured or injured bone. The present invention will indirectly measure the strain experienced by a bone and provide feed-back to the doctor.

The present invention includes one or more optical fibers embedded into a preferably composite material that is used as a supporting member of an orthopedic external fixation device.

The optical fiber can have a preferably plug type connector at each end, protruding from the composite material. At one end of the optical fiber, a laser can be attached. The light emitted by the laser can be transmitted through the embedded optical fiber to the opposite end portion thereof where a photoelectric sensor or the like can be attached to measure the light intensity. The amount of light intensity will correspond to the amount of strain experienced by the composite material.

An example of an application of this technique would be an optical fiber embedded into a hexagonally shaped bar of composite material that supports pins that are affixed to the patient's bone above and below a fracture site or osteotomy site. At the beginning of the treatment, all the weight of the patient is transferred from the bone through the pins, to the composite hex bar and back to the bone thus bypassing the fracture site.

As the doctor connects the diagnostic equipment and measures the laser light, initially he sees a low light intensity because the strain in the hex bar bends the fiber optic strand and diffuses the laser light.

After the bone has healed, the weight of the patient transfers through the bone instead of the hex bar. The light intensity is then brighter because the optical fiber would not be deformed. The doctor would then know the ideal time to remove the fixation device, because the doctor would know the light transmission value for the undeformed optical fiber.

In one embodiment, the fracture consolidation measuring apparatus is in the form of an implantable device that can be implanted, for example, in the intramedullary canal of the patient. The apparatus includes an elongated implant body in the form of an intramedullary rod. The intramedullary rod can be attached to the bone above and below the fracture. One or more optical fibers can be carried by the intramedullary rod within a bore of the rod, the optical fiber extending down the center of the bore.

A light source is positioned at one end of the optical fiber for transmitting light through the fiber. A light sensor provides a measuring device for measuring light intensity that is transmitted through the fiber. The intramedullary rod structure can be attached with bone screws at openings provided at opposing ends of the intramedullary rod. For example, the intramedullary rod can provide an enlarged upper head portion having diagonally extending holes through which bone screws can pass when the enlarged head is to be attached to a femur at the proximal end of the femur. The opposite or distal end of the rod can have transversely extending openings that receive bone screws for affixing the distal end of the intramedullary rod to the patient's distal femur.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
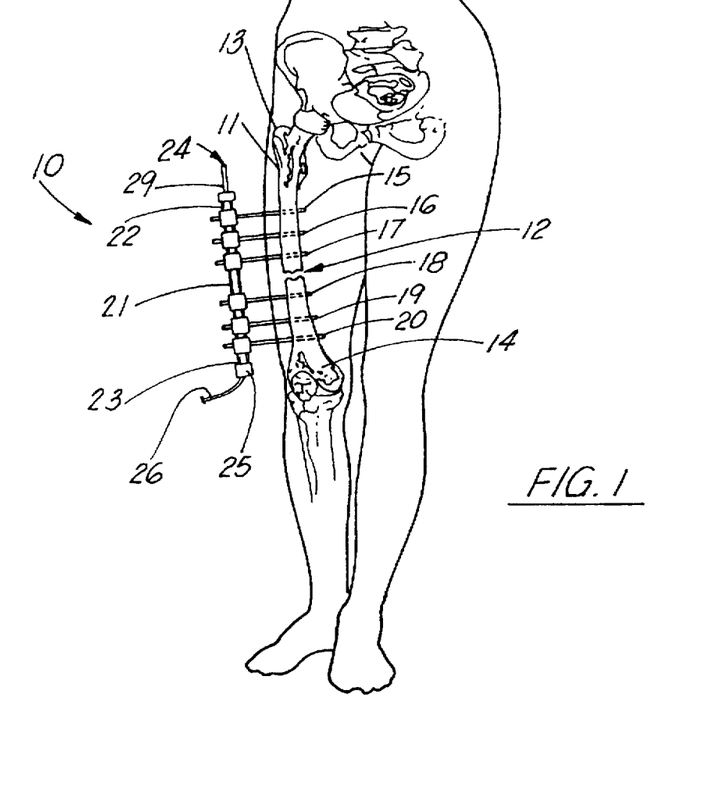
FIG. 1 is a schematic elevational view of the first and preferred embodiment of the apparatus of the present invention.
Figure 2:
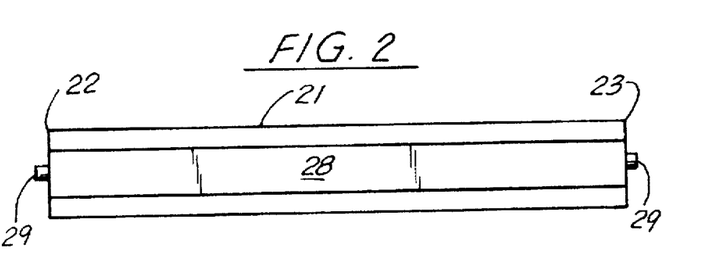
FIG. 2 is a side fragmentary view of the first embodiment of the apparatus of the present invention illustrating the composite bar portion of the external fixation device.
Figure 3:
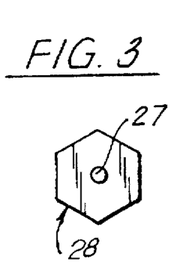
FIG. 3 is a sectional fragmentary view of the first embodiment of the apparatus of the present invention, illustrating the composite bar portion of the external fixation device.

FIGS. 1–3 show the preferred embodiment of the apparatus of the present designated generally by the numeral 10. In FIG. 1 bone strain monitor 10 is attached to a patient's femur 11 that has been fractured, the fracture site designated as 12 in FIG. 1.

The patient's femur 11 has a proximal end 13 and a distal end portion 14. A plurality of pins 15–17 are attached to one side of the femur above the fracture 12 and adjacent proximal end 13 as shown in FIG. 1. A plurality of bone pins 18–20 are attached to the portion of femur 11 adjacent distal end 14 and below fracture 12. Each of the pins 15–20 attaches to the fixation bar 21 that is shown more particularly in FIGS. 2 and 3.

Bar 21 is preferably elongated, having a proximal end 21 and a distal end 23. A laser attaches to bar 21 at 24 in such a fashion that the laser beam projects into bar 21 along a line that aligns with fiber optic cable 27. The fiber optic cable 27 has end portions 29, one of which end portions 29 receives laser beam 24. The opposite end portion of fiber optic cable 27 connects to output cable 26 that can be interfaced with a data recorder (commercially available from Newport). The data recorder (not shown) records light intensity of the laser beam as it exits and end portion 29 of fiber optic cable 27.

Bar 21 can have a hexagonal outer surface 28. Though one cable 27 is shown in FIGS. 2–3, a plurality of fiber optic cables 27 could be placed within bar 21. For example, six fiber optic cables could be positioned about the periphery of bar 21, arranged in a regular pattern, equally spaced both radially and circumferentially. Preferably, a plurality of cables are positioned at the center and near the periphery of bar 21.

Figure 4:
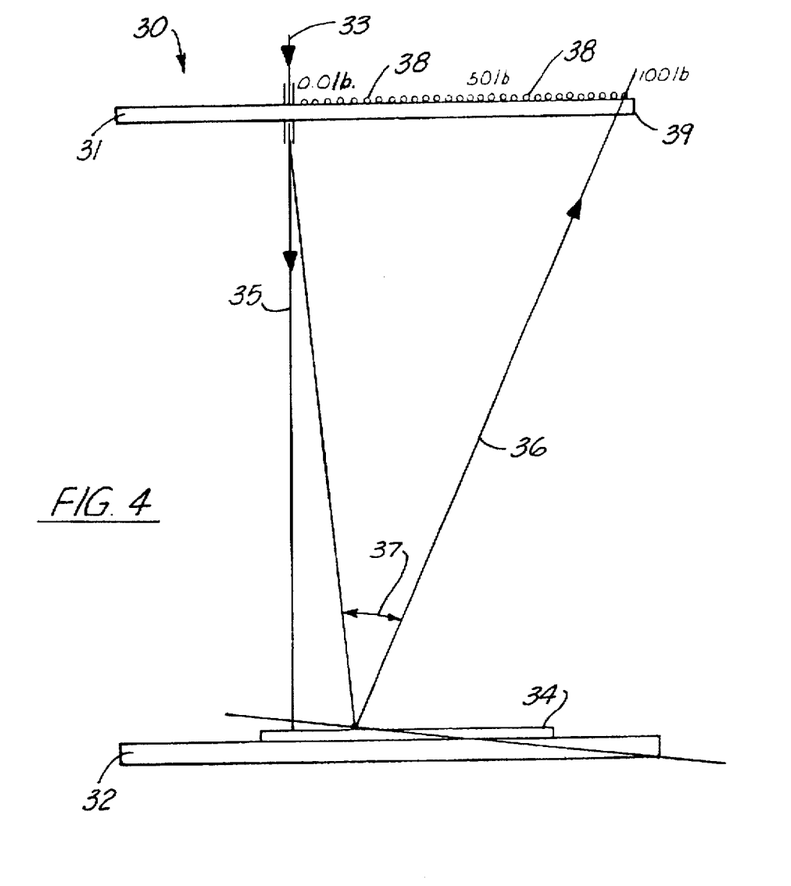
FIG. 4 is a schematic view of a second embodiment of the apparatus of the present invention.

The remaining embodiments of FIGS. 4–13 illustrate other configurations for measuring bone strain as transmitted through a pair of bone pins. In FIG. 4, designated generally by the numeral 30, a pair of pins 31, 32 are shown. Each of these pins 31, 32 would be embedded in the patient's femur 11, respectively above and below the fracture 12. The pin 31 receives laser beam 33 at right angles thereto. The beam 33 travels along line 35 to reflective surface 34.

Depending upon the angular displacement of pin 32 relative to pin 31, the laser reflects angularly along line 36 as shown in FIG. 4. The beams 35 and 36 define an angle 37 therebetween. Graduations 38 are placed along pin 31, each of the graduations defining a load value that corresponds to the load being carried by the fixation bar 21 and thus by the bone 11. When the angle 37 is minimized, the beams 35 and 36 align meaning the patient's bone has healed and is carrying all of the load.

Figure 5:
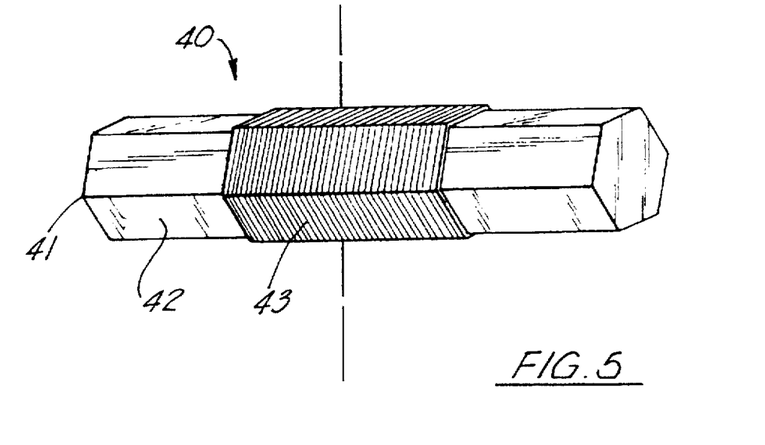
FIG. 5 is a partial perspective view of a third embodiment of the apparatus of the present invention.

In FIG. 5, the bone strain monitor is designated generally by the numeral 40. In FIG. 5, a bar 41 having a hexagonal out of surface 42 carries an outer photoelastic coating 43. The photoelastic coating 43 allows the user to view strain lines on the coating and to photograph same if desired. When the photoelastic coating does not show strain lines, the bar no longer carries load, the load being carried by the patient's bone indicating that healing has been completed.

Figure 6:
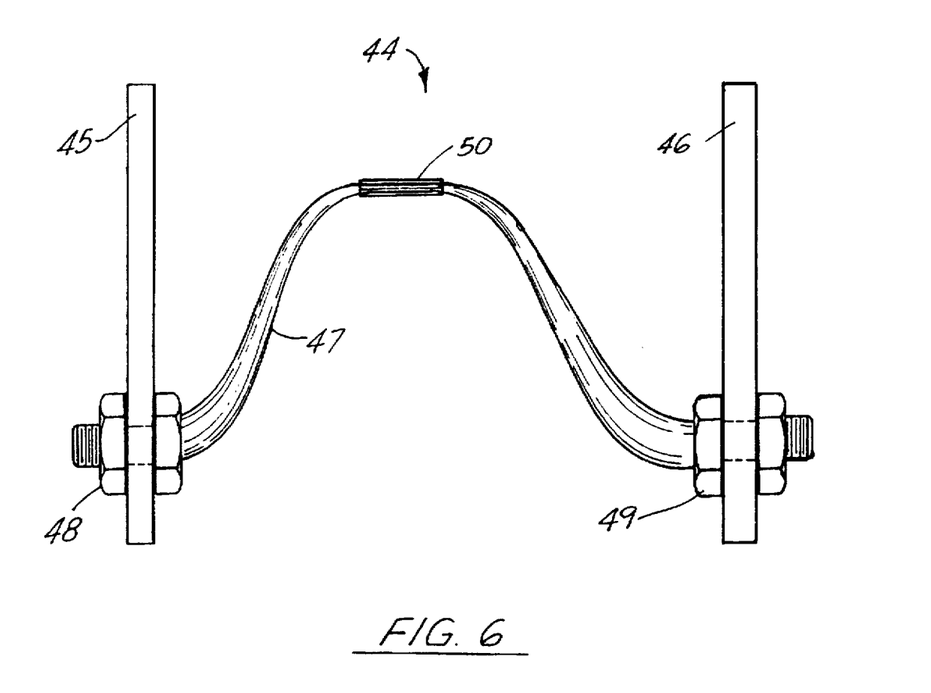
FIG. 6 is a schematic view of a fourth embodiment of the apparatus of the present invention.

FIGS. 6–9 and 13 show other variations of the photoelastic coating as part of a bone strain monitor. In the embodiment of FIG. 6, designated generally by the numeral 44, a pair of pins 45, 46 are shown connected to a U-shaped member 47. The U-shaped member attaches at 48 and 49 to the pins 45, 46 respectively. A photoelastic coating is placed at 50 for demonstrating when the pins are deflected relative to one another thus demonstrating that the bar is carrying load. When the photoelastic coating 50 shows that no strain is being carried by the bar, the patient's bone has healed and is carrying all the load.

Figure 7:
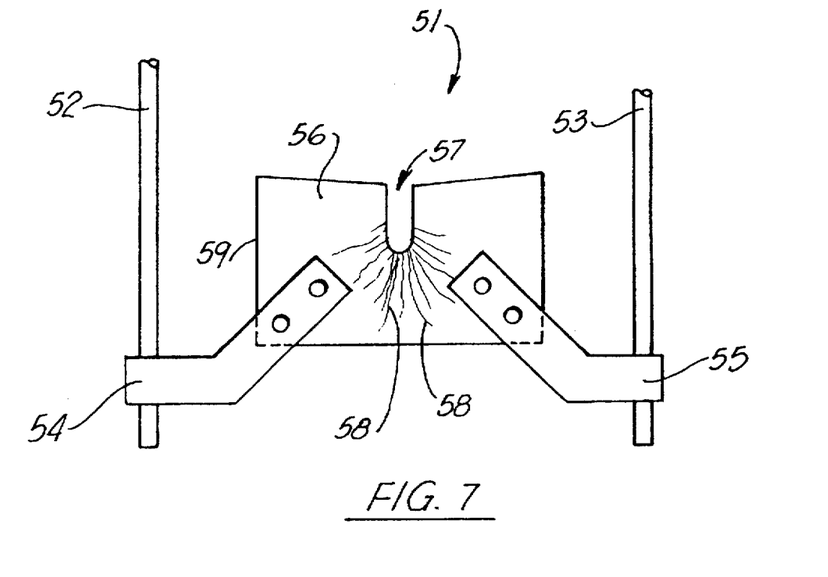
FIG. 7 is a schematic view of a fifth embodiment of the apparatus of the present invention.

In the embodiment of FIG. 7, designated generally by the numeral 51, a pair of pins 52, 53 are shown, each connecting to a support member 54, 55 respectively. The support members 54, 55 attach to plate 56 that has a photoelastic coating thereon. The plate can have a gap 57 and a periphery 59. This configuration creates easily viewed and photographed strain lines 58 that amplify an load carried by the bar as opposed to the patient's bone. When the strain lines 58 disappear, the patient's bone has healed and is carrying all of the load.

Figure 8:
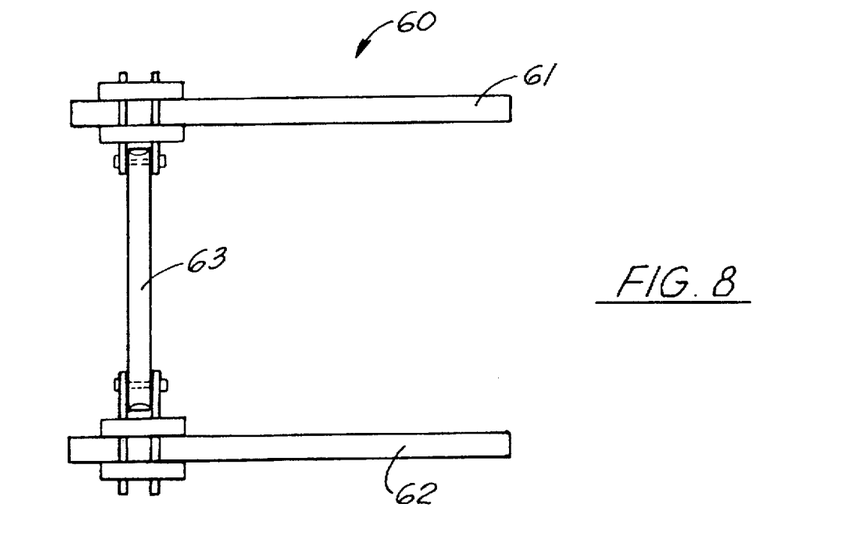
FIG. 8 is a schematic view of a sixth embodiment of the apparatus of the present invention.
Figure 9:
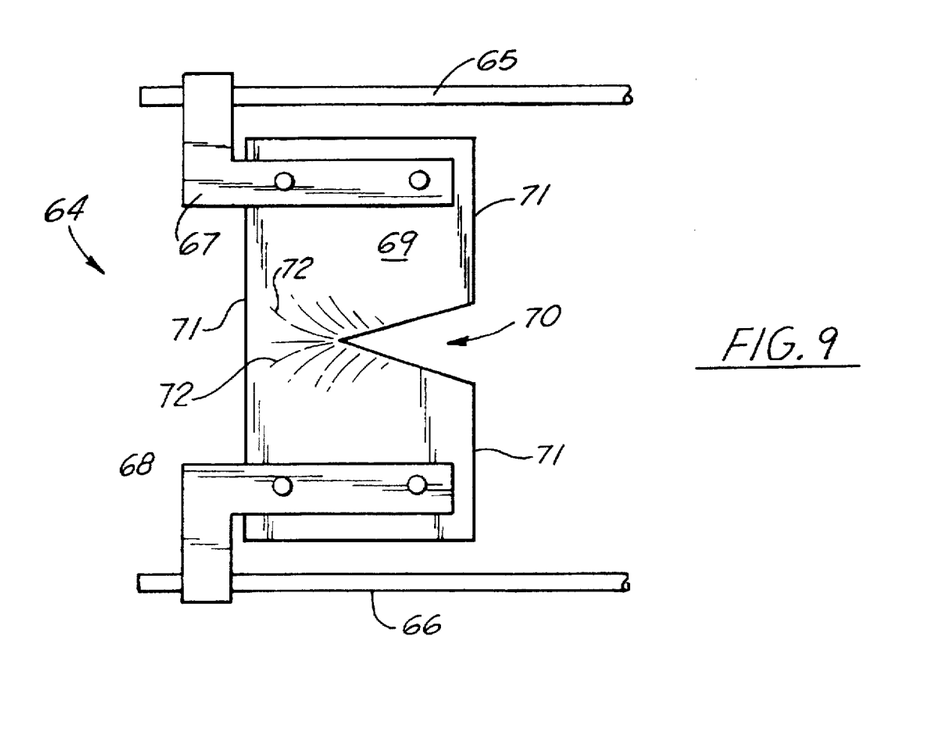
FIG. 9 is a schematic view of a seventh embodiment of the apparatus of the present invention.

In the embodiments of FIGS. 8 and 9 (designate respectively by numerals 60 and 64) photoelastic members are used. In FIG. 8, a pair of pins 61, 62 attach to a photoelastic clear plastic rod 63. In FIG. 9, pins 65, 66 attach to member 67, 68 that support plate 69. The plate 69 has a recess that is generally V-shaped at 70 and a periphery 71. The strain lines 72 are shown extending away from the V-shaped portion 70.

Figure 10:
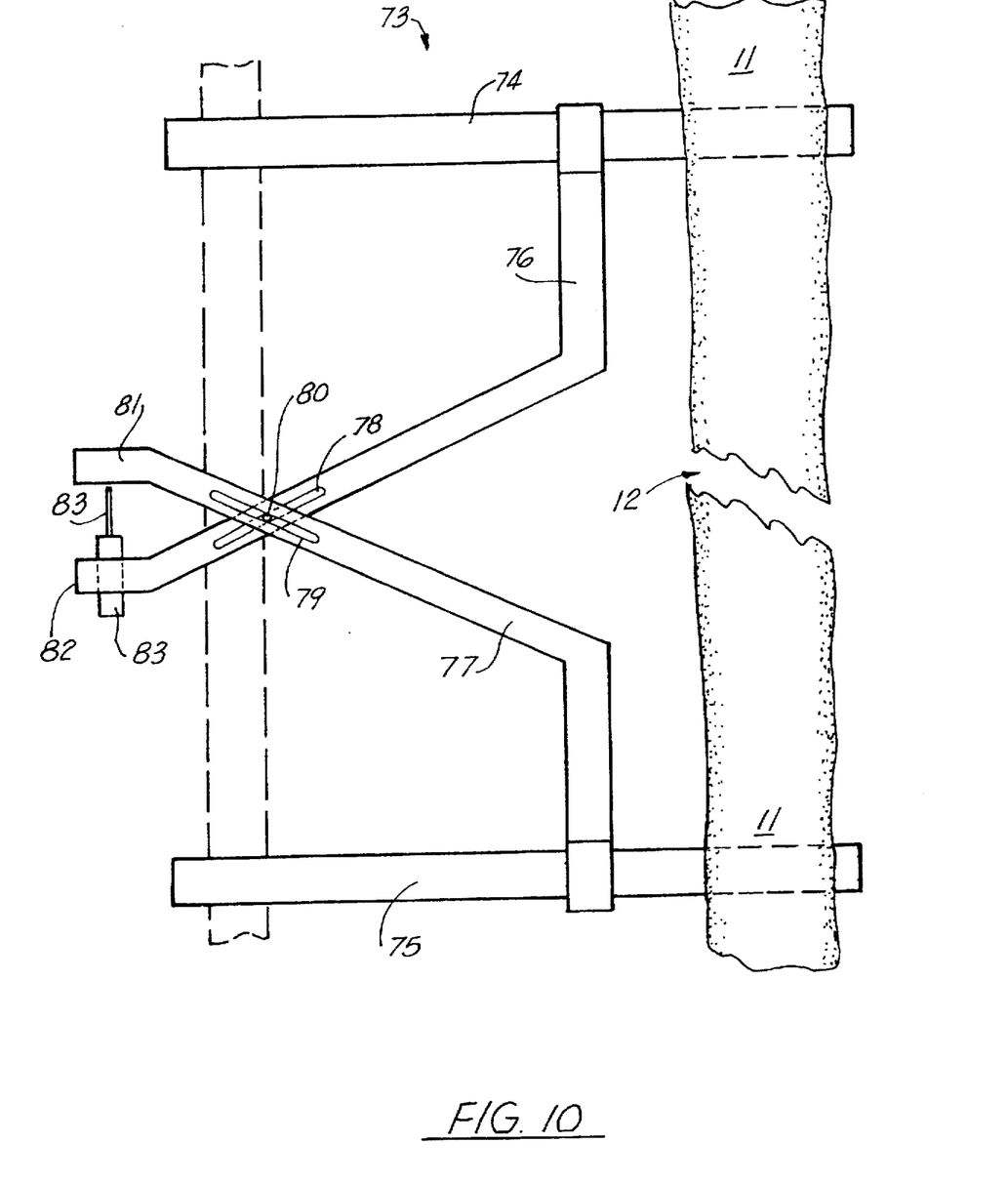
FIG. 10 is a schematic view of an eighth embodiment of the apparatus of the present invention.

In FIG. 10, designated generally by the numeral 73, a linear variable differential transducer is shown. If there is a small gap at the fracture site 12, the pins will bend toward the horizontal axis passing through the fracture site, which puts the hexagonal bar in constant bending moment.

Linear variable differential transducer placed near the soft tissue can measure accurately how much the distance between the pins is shortened. This measurement can correspond to the amount of load that is being transferred to the pins by a pair of segments that support the linear variable differential transducer. The reduction of the gap closer means that the loads are decreasing when the pins and thus the bone is carrying the load and healing as progressing. In FIG. 13 a pair of pins 73, 75 are shown attached to femur 11 above and below fracture site 12. Each of the pins 74, 75 supports an arm 76, 77. The ends 81, 82 of the arms 76, 77 translate toward and away from each other as the pins carry load. The linear variable differential transducer 83 extends between the end portions 81, 82. A gap exists between the end portions 81, 82. The reduction of the gap means that loads are decreasing on the pins, thus the bone 11 is carrying the load and healing is progressing. Other embodiment that employ a linear variable differential transducer are shown in FIG. 11 (designated by the numeral 84) and FIG. 12 (designated by the numeral 92).

Figure 11:
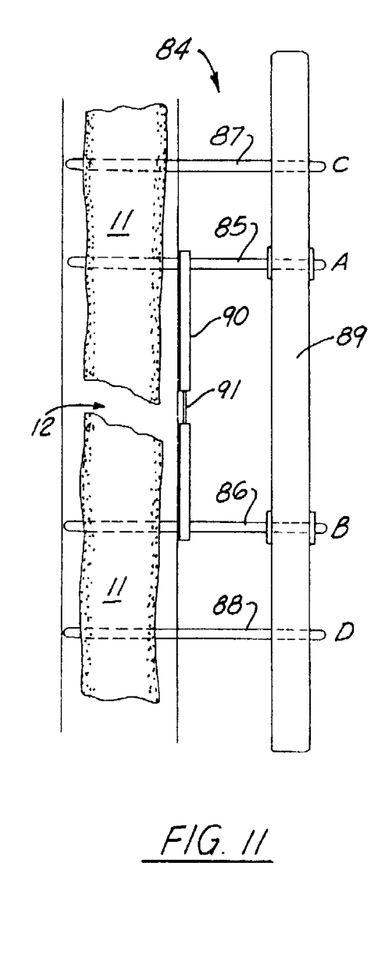
FIGS. 11–12 are schematic elevational views of a ninth embodiment of the apparatus of the present invention.

In FIG. 11, the femur 11 and fracture site 12 are shown. A pair of pins 85, 86 are disposed adjacent fracture 12 but above and below fracture 12 respectively. A second pair of pins 87, 88 are spaced further away from the fracture site 12 and above and below the fracture site respectively. Linear variable differential transducer 90 includes a gap portion 91. The pins 85–88 are attached to bar 89 as shown.

Figure 12:
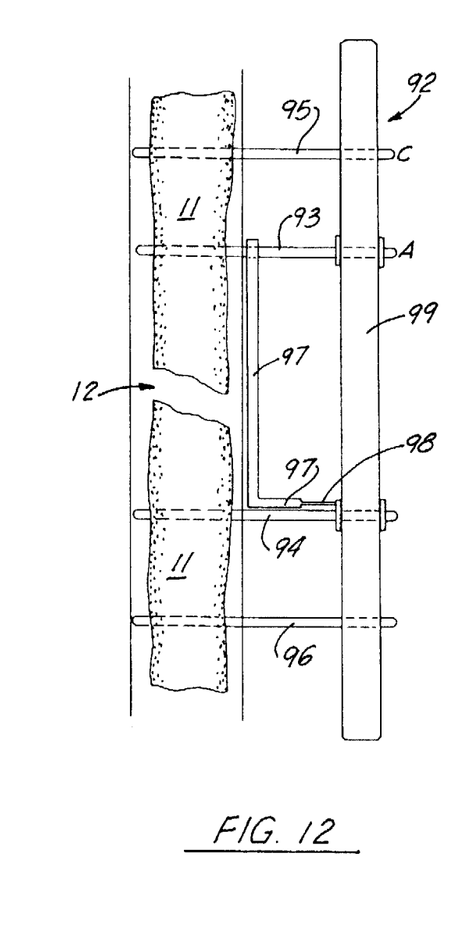
Figure 13:
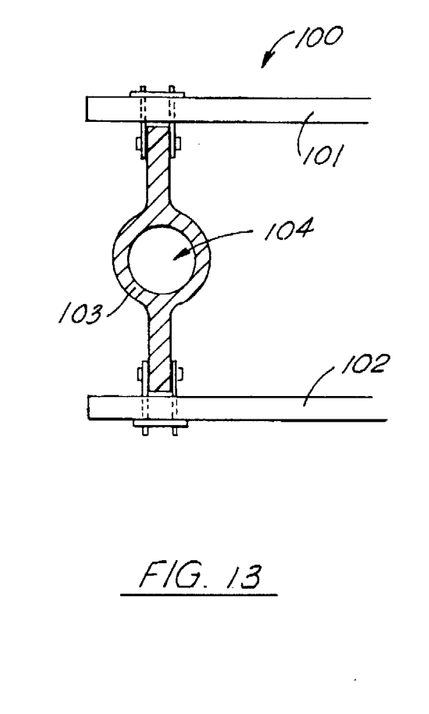
FIG. 13 is an schematic view of a tenth embodiment of the apparatus of the present invention.

In the embodiment of FIG. 12 designated by the numeral 92, the femur 11 supports pins 93–96 above and below the gap as shown in the drawing. Each of the pins 93–96 is also attached to the bar 99. The linear variable differential transducer 97 is generally L-shaped, being rigidly attached to the pin 93 and including a gap 98. Each of the embodiments of FIGS. 11 and 12, reduction of the gap means that loads are decreasing on the pins, thus the bone is carrying the loads and healing is progressing.

FIG. 13 illustrates a further embodiment designated generally by the numeral 100. In FIG. 13, a pair of pins 101, 102 are attached to member 103 having a circular opening 104. The member 103 carries a photoelastic coating that shows strain lines if the pins 101, 102 carry bending moment thus indicating that the bone is transmitting the load to the member 103.

Figure 14:
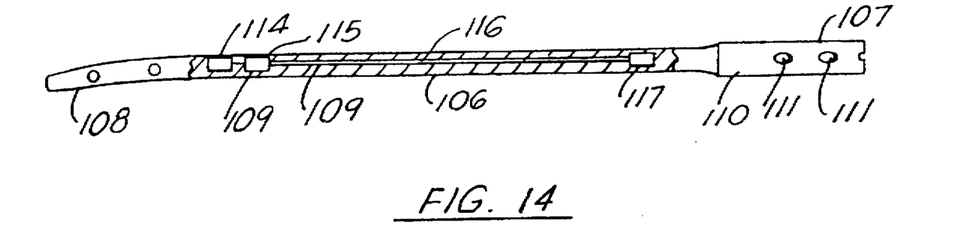
FIG. 14 is a partial section view of an eleventh embodiment of the apparatus of the present invention.
Figure 15:
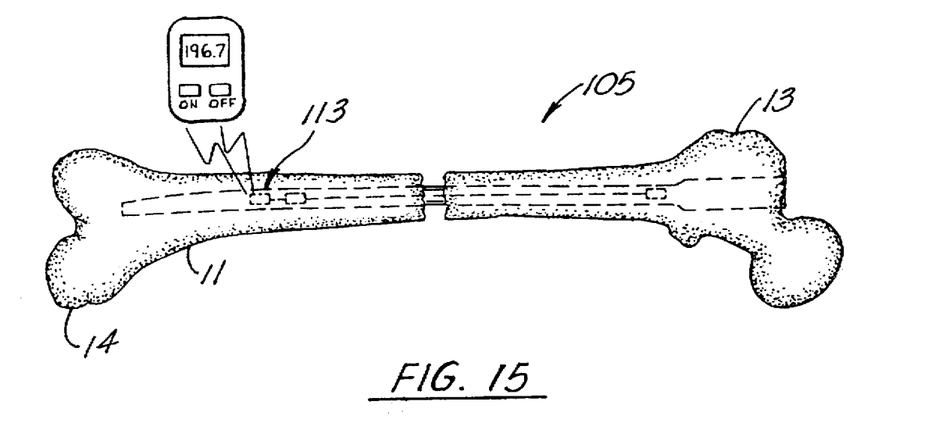
FIG. 15 is a schematic view of the eleventh embodiment of the apparatus of the present invention.
Figure 16:
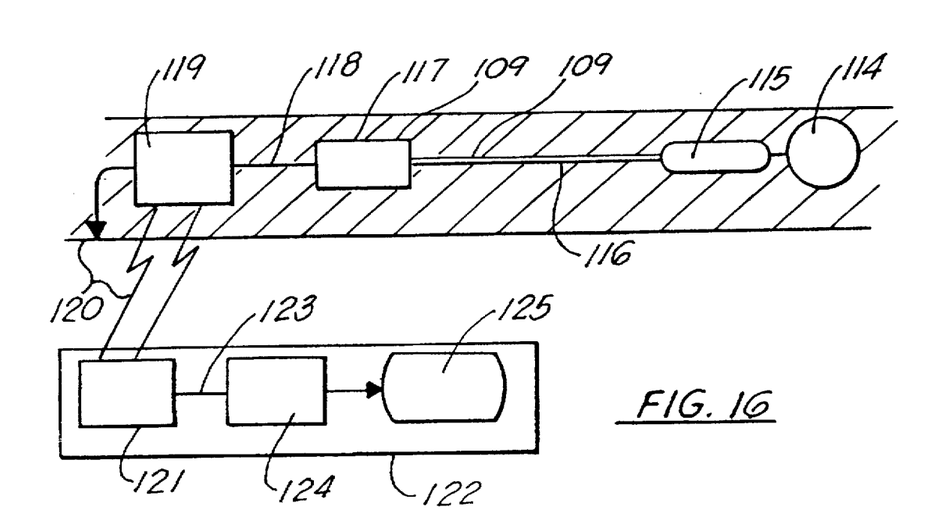
FIG. 16 is a partial schematic diagram of the eleventh embodiment of the apparatus of the present invention.

FIGS. 14–16 illustrate the eleventh embodiment of the apparatus of the present invention designated generally by the numeral 105 in FIG. 15. The bone strain monitor apparatus 105 includes an elongated intramedullary nail 106 having a proximal head 107 at its proximal end and a distal 108 end portion. The intramedullary rod 106 can have an elongated bore that carries bone strain monitor components, the bore being designated by the numeral 109.

The proximal end 107 has an enlarged head 110 that can carry openings 111 for affixing the intramedullary rod 106 to the patient's femur 11. The distal end 108 can likewise have openings 112 for affixing the distal end 108 of rod 106 to the patient's femur.

FIG. 15 shows the rod 106 implanted within the femur 11 of a patient. The rod positioned within the intramedullary canal of femur 11 is shown in phantom lines in FIG. 15, the numeral 113 indicating the intramedullary canal. The intramedullary nail 106 is preferably of a composite material but could be of metallic construction, such as titanium, for example.

In FIGS. 14 and 16, bone strain monitor apparatus 105 includes a power source such as battery 114 that energizes a light source 115. The light source 115 is positioned at one end of optical fiber 116 for transmitting light through the optical fiber 116 between light source 115 and light sensor 117. In FIG. 16, the photo sensor or light sensor 117 is shown as connected via cable 118 to modulator. The cable 118 carries a VC analog signal from photo sensor to modulator 119. The modulator 119 then generates a wireless FM signal designated generally by the arrows 120 that is received by demodulator 121 of receiver 122. The demodulator 121 is connected via cable 123 to analog/digital converter 124 that communicates with liquid crystal display 125.

The battery 114 provides the power for the light source 115 which can be a light emitting diode. The light source or light emitting diode 115 transmits light through optical fiber 116. The sensor 117 can be a photovoltaic sensor at the opposing end of the fiber 116 from light source 115. One or more fibers 116 can be provided. The fiber or fibers 116 measure the intensity of the light and sends current to the modulator 119 which converts the analog input to an FM signal that is transmitted from within the body of the rod 106 to a receiver 122 such as hand-held receiver. The receiver 122 contains the demodulator 121 for converting the FM signal back to an analog signal. Analog digital converter 124 provides a digital output to display 125, preferably a liquid crystal display (LCD) which is then read by the doctor. Amplifiers may also be used to boost the signals. The implant rod 106 components are thus fully encapsulated within the implant 106 and thus are protected from the environment of the body.

Figure 17:
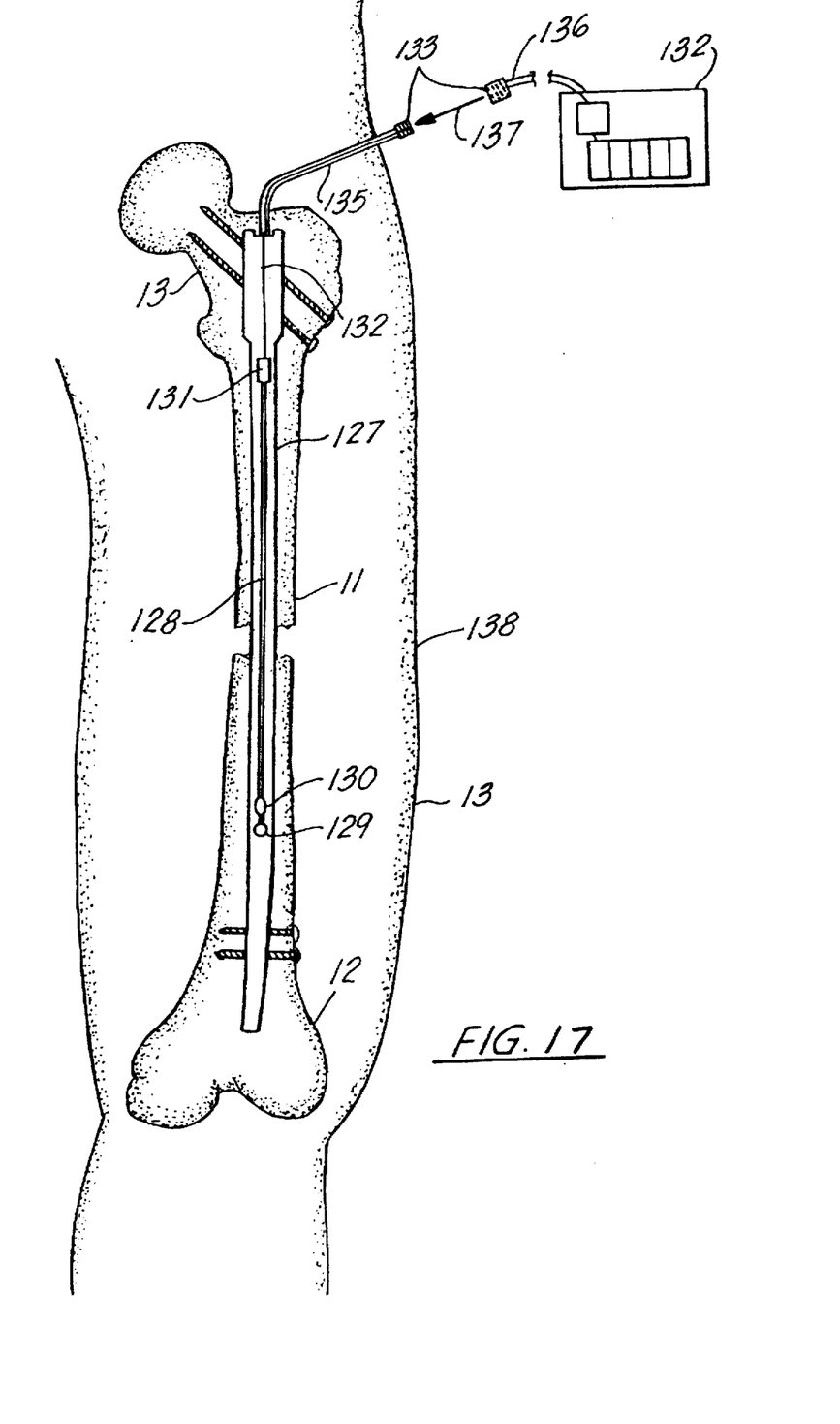
FIG. 17 is a schematic elevation view of a twelfth embodiment of the present invention.

FIG. 17 shows a twelfth embodiment of the apparatus of the present invention designated generally by the numeral 126. In the embodiment of FIG. 17, the femur 11 carries intramedullary rod 127 having an optical fiber 128. As with the embodiment of FIGS. 14–16, a battery 129 is used to power light source 130 for transmitting light through optic fiber 128 to sensor 131. In the embodiment of FIG. 17, a cable 132 is used to transfer light intensity information from light sensor 131 to display 134. A quick connect coupling 133 can be used to connect cable sections 135, 136 as shown by the arrow 137 in FIG. 17. The cable sector 135 thus extends externally of the patient's leg 138 in the embodiment of FIG. 17.

The following table lists the part numbers and part descriptions as used herein and in the drawings attached hereto.

PARTS LIST

| Part Number | Description |
| --- | --- |
| 10 | bone strain monitor |
| 11 | femur |
| 12 | fracture |
| 13 | proximal femur |
| 14 | distal femur |
| 15 | pin |
| 16 | pin |
| 17 | pin |
| 18 | pin |
| 19 | pin |
| 20 | pin |
| 21 | bar |
| 22 | proximal end |
| 23 | distal end |
| 24 | laser |
| 25 | light sensor |
| 26 | output cable |
| 27 | fiber optic cable |
| 28 | hexagonal outer surface |
| 29 | end portion |
| 30 | bone strain monitor |
| 31 | pin |
| 32 | pin |
| 33 | laser beam |
| 34 | reflecting surface |
| 35 | first line |
| 36 | second line |
| 37 | angle |
| 38 | graduation |
| 39 | maximum deflection |
| 40 | bone strain monitor |
| 41 | bar |
| 42 | hexagonal outer surface |
| 43 | photoelastic coating |
| 44 | bone strain monitor |
| 45 | pin |
| 46 | pin |
| 47 | U-shaped member |
| 48 | attachment |
| 49 | attachment |
| 50 | photoelastic coating |
| 51 | bone strain monitor |
| 52 | pin |
| 53 | pin |
| 54 | support |
| 55 | support |
| 56 | plate |
| 57 | recess |
| 58 | strain lines |
| 59 | periphery |
| 60 | bone strain monitor |
| 61 | pin |
| 62 | pin |
| 63 | rod |
| 64 | bone strain monitor |
| 65 | pin |
| 66 | pin |
| 67 | support |
| 68 | support |
| 69 | plate |
| 70 | recess |
| 71 | periphery |
| 72 | strain lines |
| 73 | bone strain monitor |
| 74 | pin |
| 75 | pin |
| 76 | support |

-continued

PARTS LIST

| Part Number | Description |
| --- | --- |
| 77 | support |
| 78 | slot |
| 79 | slot |
| 80 | pin |
| 81 | end |
| 82 | end |
| 83 | transducer |
| 84 | bone strain monitor |
| 85 | pin |
| 86 | pin |
| 87 | pin |
| 88 | pin |
| 89 | bar |
| 90 | transducer |
| 91 | gap |
| 92 | bone strain monitor |
| 93 | pin |
| 94 | pin |
| 95 | pin |
| 96 | pin |
| 97 | transducer |
| 98 | gap |
| 99 | bar |
| 100 | bone strain monitor |
| 101 | pin |
| 102 | pin |
| 103 | photoelastic member |
| 104 | circular opening |
| 105 | bone strain monitor apparatus |
| 106 | intramedullary rod |
| 107 | proximal end |
| 108 | distal end |
| 109 | bone |
| 110 | head |
| 111 | openings |
| 112 | opening |
| 113 | intramedullary canal |
| 114 | battery |
| 115 | light source |
| 116 | optical fiber |
| 117 | light sensor |
| 118 | cable |
| 119 | modulator |
| 120 | wireless signal |
| 121 | demodulator |
| 122 | receiver |
| 123 | cable |
| 124 | converter |
| 125 | display |
| 126 | bone strain monitor apparatus |
| 127 | intramedullary rod |
| 128 | optic fiber |
| 129 | battery |
| 130 | light source |
| 131 | light sensor |
| 132 | cable |
| 133 | connection |
| 134 | display |
| 135 | cable section |
| 136 | cable section |
| 137 | arrow |
| 138 | patient's leg |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A fracture consolidation measurement device for determining when a patient's bone has healed at a bone fracture or bone defect, comprising:
   a) an elongated instrument body having an axis that can be placed in a generally aligned position with the axis of the bone to be healed;
   b) first and second attachments that extend between the bone to be healed and the instrument body, said attachments forming connections with the bone to be healed at positions that are spaced away from the bone fracture or defect so that the attachments do not interfere with the healing process at the fracture or bone defect;
   c) one or more optical fiber sensors carried by the instrument body for transmitting light along the instrument body between first and second positions that are adjacent to the first and second attachments;
   d) a measuring device for measuring light intensity that is transmitted through the optical fiber sensor as an indication of strain within the instrument body during the healing process; and
   e) the attachments and instrument body defining a structure that can carry all or substantially all of the load on the bone thus bypassing the fracture or defect until healing is complete.

2. The fracture consolidation measurement apparatus of claim 1 wherein the measurement device includes a light source positioned at one end of the optical fiber sensor to transmit light to the optical fiber sensor at said end.

3. The fracture consolidation measurement apparatus of claim 1 further comprising a light sensor positioned generally opposite the light source, at an opposite end portion of the optical fiber sensor.

4. The fracture consolidation measurement apparatus of claim 1 further comprising a transmitter for transmitting a signal from the light sensor to a receiver, and a receiver for displaying a light intensity value.

5. The fracture consolidation measurement apparatus of claim 4 further comprising a cable that connects the transmitter and receiver.

6. The fracture consolidation measurement apparatus of claim 4 wherein a wireless airwave signal is transmitted by the transmitter and received by the receiver.

7. The fracture consolidation measurement apparatus of claim 1 wherein the body is an instrument mounted externally of the bone that is to be healed.

8. The fracture consolidation measurement apparatus of claim 1 wherein the body is an instrument mounted externally of the bone that is to be healed, and the attachments comprise a plurality of bone pins forming attachments between the instrument body and the bone to be healed.

9. The fracture consolidation measurement apparatus of claim 1 wherein the body is an instrument mounted externally of the bone that is to be healed, and the attachments comprise a plurality of bone pins forming attachments between the instrument body and the bone to be healed at positions on both sides of the fracture or bone defect.

10. A fracture consolidation measurement apparatus for determining when a patient's bone has healed at a bone fracture or bone defect, comprising:
    a) an elongated body having an axis that can be placed in a generally aligned position with the axis of the bone to be healed;
    b) first and second attachments that pass through the bone to be healed and connected to the body, said attachments forming connections with the bone to be healed at positions that are spaced away from the bone fracture or defect so that the attachments do not interfere with the healing process;
    c) one or more optical fiber sensors carried by the instrument body for transmitting light along the instrument body between first and second positions that are adjacent to the first and second attachments;
    d) a measuring device for measuring light intensity that is transmitted through the fiber as an indication of strain within the instrument body during the healing process; and
    e) the attachments and instrument body defining a structure that can carry all or substantially all of the load on the bone.

11. The fracture consolidation measurement apparatus of claim 10 wherein the body is an implantable intramedullary rod mounted within the intramedullary canal of the bone to be healed.

12. The fracture consolidation measurement apparatus of claim 11 wherein the body is an implantable intramedullary rod having a hollow bore.

13. The fracture consolidation measurement apparatus of claim 12 wherein the optical fiber occupies the bore.

14. The fracture consolidation measurement apparatus of claim 13 wherein the bore has a light source for transmitting light through the optical fiber.

15. The apparatus of claim 10 further comprising a light source that transmits light to the body.

16. The fracture consolidation measurement apparatus of claim 1 wherein the instrument body includes a surgically implantable structure.

17. The fracture consolidation measurement apparatus of claim 16 wherein the instrument body includes a surgically implantable structure that can be implanted in a patient's bone intramedullary canal.

18. The fracture consolidation measurement apparatus of claim 16 wherein the structure includes an intramedullary nail.

19. The fracture consolidation measurement apparatus of claim 1 wherein the body is an implantable intramedullary rod having a hollow bore.

20. The fracture consolidation measurement apparatus of claim 19 wherein the optical fiber sensor occupies the bore.

* * * * *